United States Patent [19]
Fuson et al.

[11] 3,957,082
[45] May 18, 1976

[54] SIX-WAY STOPCOCK

[75] Inventors: Robert Lee Fuson, North Branch, N.J.; Wesley S. Larson, Enfield, Conn.

[73] Assignee: Arbrook, Inc., Arlington, Tex.

[22] Filed: Sept. 26, 1974

[21] Appl. No.: 509,363

[52] U.S. Cl. .................. 137/625.41; 128/214 B; 128/214 R; 128/274; 128/DIG. 26
[51] Int. Cl.² ........................................ F16K 11/02
[58] Field of Search ............... 137/625.11, 625.41, 137/625.47; 128/214 B, 214 R, 274, DIG. 26

[56] References Cited
UNITED STATES PATENTS

| 2,077,774 | 4/1937 | Rudder | 128/214 B |
| 2,261,213 | 11/1941 | Bierman | 128/DIG. 26 |
| 2,335,085 | 11/1943 | Roberts | 137/625.11 |
| 2,964,056 | 12/1960 | Speer | 137/625.47 X |
| 3,626,938 | 12/1971 | Versaci | 128/274 |
| 3,773,078 | 11/1973 | Suntheimer | 137/625.11 |
| 3,794,032 | 2/1974 | Derouineau | 128/274 |
| 3,834,372 | 9/1974 | Turney | 128/274 X |

Primary Examiner—Henry T. Klinksiek
Attorney, Agent, or Firm—John J. Simkanich

[57] ABSTRACT

A selection valve, creating a minimal flow-through turbulence for use in the administration of three separately supplied intravenous fluids, for selecting with one-handed operation any one of the fluids connected or a mixture of any two fluids adjacently connected, is provided having a body with a cylindrically shaped cavity containing three closely positioned ports and a separately positioned port. A cylindrically shaped rotor may be disposed within the cavity and rotated to position a single passageway part thereof between the outlet and an inlet port. The outlet end of the passageway may be shaped to enable the exposure of the outlet port for any inlet port position. Preferably the valve body is mounted to a support structure which in turn may be secured to an immobile surface.

16 Claims, 8 Drawing Figures

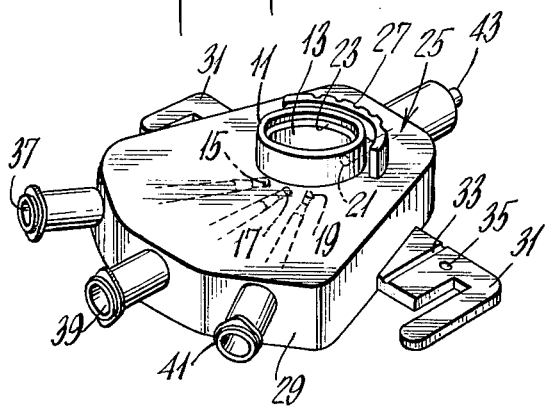

SIX-WAY STOPCOCK

BACKGROUND OF THE INVENTION

Medical technology in dealing with the intravenous injection of drugs and solutions has undergone rapid and significant changes in recent years. Today an anesthesiologist may desire to administer two or more solutions to a patient during operative and postoperative procedures. These solutions may include not only blood, plasma and saline but any of the drugs needed by the patient.

In order to minimize the shock imposed upon a patient by the repeated insertions of hypodermic needles, to minimize blood loss and to minimize the chances of infection, a multiple-solution intravenous procedure has been developed whereby all fluids are fed to the patient through a single hypodermic needle.

Fluid flow to this needle is controlled by a valve or stopcock. Fluid supplies are connected to the valve's inlets and the valve is operated to feed one of the fluids to the needle. An "off" position may be present in which all valve ports are closed thereby stopping fluid flow to the patient while minimizing blood loss by the patient.

Stopcock valves available in the prior art are usually made of non-toxic nylon or polypropylene and polyethylene plastics. These valves have always been quite small and have required two hands to operate. Additionally, they may hang supported by the fluid tubing.

Some of these valves operated by rotating a cylindrical gating mechanism in which there are passageways for the flow of fluids from inlet to outlet. Some valves were designed to gate three fluids, but often had their inlet ports spaced 60° to 90° apart to allow space for tubing connection apparatus. As a result, passageways in these valves were quite complicated, often creating acute changes in direction of flow of fluid passing through them. Right angle turns and protrusions into the fluid path were common. These prior art valve designs tended to introduce turbulences into the intravenous fluids as the fluids passed through the valve. This ultimately may result in blood damage to the patient.

Additionally, these prior stopcocks have been difficult to operate precisely. Very few of them included any sort of positive retaining mechanism corresponding to a particular valve state. All must be looked at when the valve is operated in order to tell what position the valve is in.

It is desirable to have a valve which is easily operated, which has definite positions, which may be tactilly operated with one hand, and which minimizes turbulence introduced into the intravenous fluid. It is also desirable to have a valve which is more versatile than those currently available.

An object of this invention, therefore, is to provide an intravenous fluid valve which minimizes turbulence added to the intravenous fluids passing through it.

Another object of this invention is to provide a valve which may be operated tactilly, with one hand.

A further object of this invention is to provide a valve operation that is easily discernable and which has positive positions.

An additional objective of this invention is to provide a six-way valve which can feed any of three connected fluids solely, or can feed a mixture of any two adjacently connected fluids or can be turned completely off, sealing off the patient's blood system.

A further object of this invention is to provide apparatus for sealing inlet ports when they are not in use.

SUMMARY OF THE INVENTION

The objectives of the invention are achieved by a six-way stopcock which may be used among other things for controlling the feeding of three intravenous fluids to a patient. Three separate supplies are individually connected to the stopcock valve and a single tube feeds an intravenous hypodermic needle or intravenous catheter.

The valve may include a body having a cylindrical cavity and extending therethrough three closely positioned ports which may be used as inlets and a separately positioned port, which may be used as an outlet. A cylindrically shaped rotatable gating member may be disposed with a tight fit therewithin. This rotor gating member may include a single passageway for connecting inlet to outlet ports, having a substantially straight axis and being flared at the outlet port end thereof.

Inlet ports may be spaced around a circumferential arc of the body at no greater than 30° from the next.

The valve body may be attached to a support structure. In cooperation, a support plate and a skirt member, to which the valve is attached, may hold the valve above a mounting surface. Folding tabs connected to the free end of the skirt member may be used in securing the entire apparatus to this mounting surface.

Extension tubes may be included for connecting the inlet and outlet ports to external intravenous couplings. Caps may be employed to seal inlet and outlet tubes not in use. Indicia may signify the valve positions.

DESCRIPTION OF THE DRAWINGS

The various features and advantages of this invention will become readily apparent from the following detailed description and the appended claims, read in view of the following drawings, in which like numerals refer to like parts and in which:

FIG. 2 is a perspective view of the body and support members of the stopcock.

FIG. 3 is a perspective of the rotor gate showing the detent, off position stops and outlet port end of the transverse passageway.

FIG. 7 shows a cross sectional view of an inlet port mating the rotor passageway.

FIG. 8 shows a sectional view of the relationship of between rotor valve passageway and inlet and outlet ports and the flow of fluid through the valve for a "mixture" position of the rotor valve.

DETAILED DESCRIPTION OF THE INVENTION

A six-way stopcock for use in the control of intravenous fluids can be operated with one hand by an anesthesiologist who must devote his attention to monitoring a patient's vital life signs. The valve can be positioned into six states for passing a first fluid, a second fluid, a third fluid, or a mixture of fluids 1 and 2 or fluids 2 and 3, or "off." When alternately connected the device may be utilized for pressure monitoring and sampling of fluids as well as the monitoring on bodily sounds including heart and pulse sounds.

Figure 1:
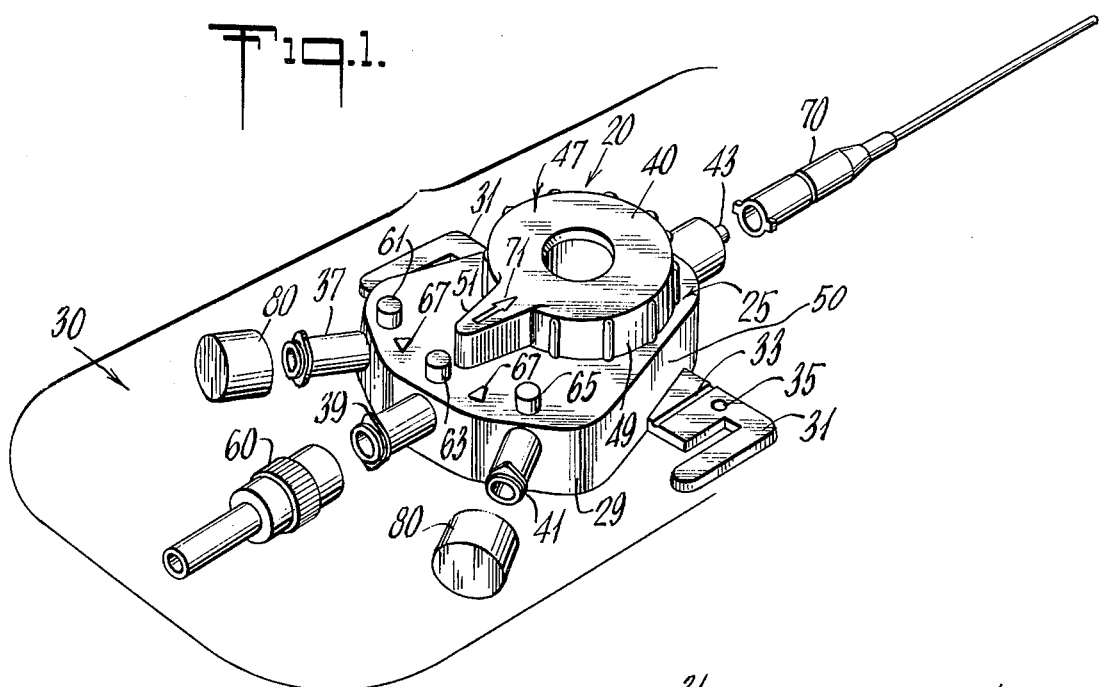
FIG. 1 is a perspective view of the stopcock.

The valve 20, is shown in FIG. 1, secured to a mounting surface such as an arm board 30. Tape, cord or safety pins may be used for this end. Valve 20 has a linear high density polyethylene rotor gate 40 disposed within a body and support member 50. Connected to the valve 20 may be fluid supply tubing 60 and intravenous tubing 70. Unused openings are sealed with the Luer fit caps 80.

More specifically, the body and support member 50, FIG. 2, has a valve body 11 having a cylindrically-shaped cavity 13. Body 11, furthermore, has an essentially flat bottom, an open top and an essentially cylindrical exterior.

Three 14-gauge or larger opening inlet ports 15, 17, 19 and a 14-gauge or larger opening outlet port 21 extend through the cylindrical wall of the body 11 a distance from the top of the cavity 13. The ports 15, 17, 19, 21, lie in a plane parallel to the top of the cavity 13 with the second inlet port 17 being positioned 30° of circumferal arc from the first port 15; the third port 19, 30° of circumferal arc from the second port 17. Outlet port 21 is located diametrically across from the second inlet port 17.

An annular groove 23 exists in the wall of cylindrical cavity 13 at a position outward from the ports 15, 17, 19, 21.

Body 11 extends, normally, through an irregular hexagon-shaped support plate 25 and is attached near the midpoint of its wall and above the ports 15, 17, 19, 21. Plate 25 is essentially flat with its top surface near to the opening of cavity 13.

Extending perpendicularly out of the top surface of the plate 25 is a curved indented retention plate 27. Retention plate 27 is semi-circular, approaching an excursion of 120°, and is positioned away from the outer wall of body 11 about a point over the outlet port 21. Retention plate 27 contains five indentations in its outer curvature each extending outwardly from the support plate 25. Three are deeper indentations, each in alignment with a radius through a separate one of the inlet ports 15, 17, 19. Two are lesser indentations, located one each midpoint between the deeper indentations.

Extending perpendicularly from the bottom surface of the support plate 25 at the outer edge of support plate 25 is a skirt member 29. The skirt 29 extends from support plate 25 a distance greater than that of body 11.

Extending outwardly from the skirt 29 on opposite sides of said skirt 29 are a pair of flexible tabs 31.

Flexible tabs 31 each include a rectangular portion which mates with the skirt 29, containing a living hinge 33 and a drilled hole 35. A L-shaped portion of the tabs 31 mates with the rectangular portion to form a L-shaped tab 31. The pair of tabs 31 are positioned symmetrically about a centerline axis of the body and support member 50.

Four connection tubes 37, 39, 41, 43 permit a connection to each of the ports 15, 17, 19, 21, respectively, at a point beyond the skirt 29. Each connection tube 37, 39, 41, 43 extends along a radial from the center of the body cavity 13 in alignment with the axis of its respective port 15, 17, 19, 21. The first three of these tubes 37, 39, 41 each have female Luer taper fittings with a flanged end for mating the threads of a Luer lock. The fourth tube 43 has a male Luer taper fitting end within a threaded Luer lock.

Rotor gate 40, FIG. 3, includes a rotor member 45 which is cylindrical in shape; the height of this cylinder approximating the depth of body cavity 13.

An operator knob 47 is situated on one end of the rotor cylinder 45. Knob 47 has a hollow round member 49 with an open bottom and a triangular-shaped finger member 51 extending outwardly from the outer circumference of the round member 49. Round member 49 and finger member 51 have essentially flat top surfaces with the finger member 51 having serrated sides and the round member 49 having a bossed outer circumference. The outer edge of the round member 49 is positioned on the outside of the retention plate 27 when the rotor gate 40 is positioned in cavity 11.

An annular ring 53 protrudes from the cylindrical outer surface of the rotor 45 at a position near the knob 47 so as to interact with the annular groove 23 when the rotor gate 40 is disposed within the body cavity 13.

A rectangular passageway 55 diametrically transverses the rotor 45 perpendicular to the cylindrical walls of the rotor at a location lying in the plane of the ports 15, 17, 19, 21 when the rotor gate 40 is positioned within the cavity 13. The passageway 55 has a substantially straight axis parallel to the centerline of the finger 51. The height of the passageway 55 is uniform across the rotor 45 and is equal to the diameter of the ports 15, 17, 19, 21. The width of the passageway 55, at the finger 51 side of the rotor 45, defines an opening of at most 30° on a circumferential arc of the rotor 45 wall. This width remains constant through the rotor 45 to a point near the side opposite the finger 51 where it flares to a width defining an opening of at most 60° of circumferential arc of the rotor 45 wall. The distance at which the passageway 55 flare begins may be nearly three-fourths the diameter of the rotor 45.

A detent plate 57 extends inwardly from the inside surface of the hollow round member 49 to engage the indentations of the retention plate 27 when the rotor gate 40 is disposed within the cavity 13. The extension of the detent 57 is aligned with the axis of the passageway 55.

A pair of stop plates 59 extend inwardly from the inside surface of the hollow round member 49. Each of the stop plates 59 is positioned 120° on a circumferential arc from the detent 57 and has an extension large enough to abut the end of curved retention plate 27 when the knob 47 is rotated, the rotor gate 40 being in position within the cavity 13.

Figure 4:
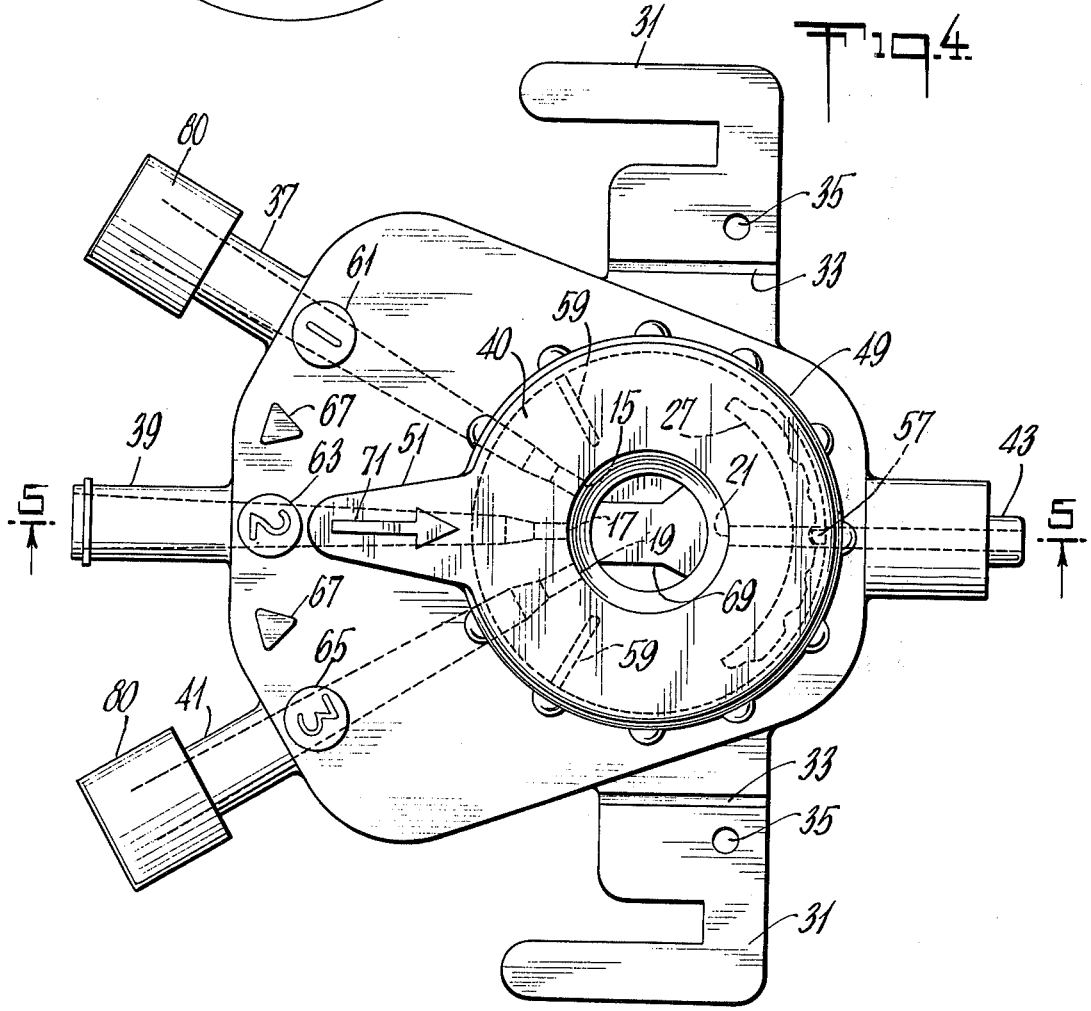
FIG. 4 is a plan view of the stopcock showing the rotor valve in position and the operating indicia.

Indicia signifying the stopcock's operational states are mounted on the top surface of the support plate 25, FIG. 4, and on the top surface of the rotor gate's knob 47.

A raised numeral "one" 61 is located above connection tube 37, on support plate 25. Similarly, the raised numerals "two" 63 and "three" 65 are located above tubes 39 and 41 respectively. Located midpoint between the numerals "one" and "two" and the numerals "two" and "three" are raised diamond-shaped indicators 67.

The top of the knob 47 is excavated to a depth slightly greater than that of the passageway 55 leaving the walls of the passageway 55 intact but exposing the shape 69 and position of the passageway 55 with respect to the rotor 45 and the knob 47.

An "arrow" 71, which points the direction of flow, is embossed on top of the finger member 51 pointing to the center of the knob 47.

Figure 5:
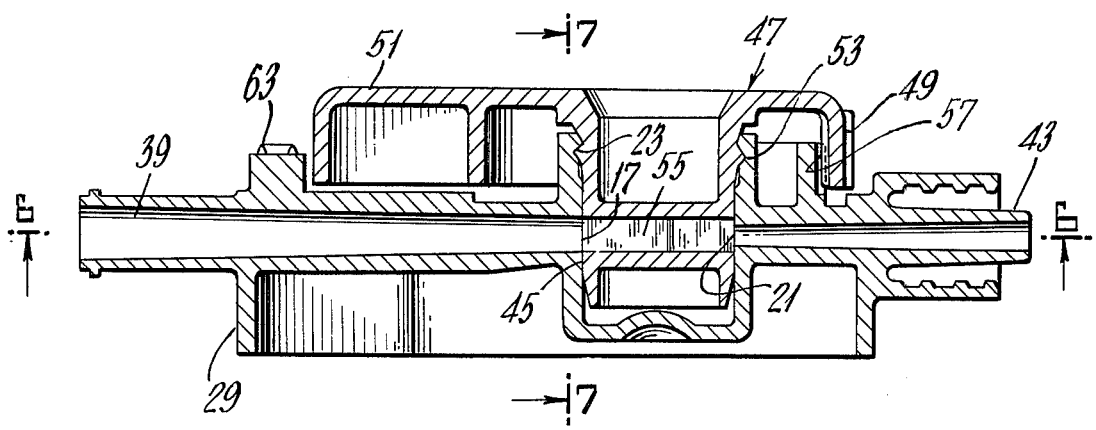
FIG. 5 is a sectional view of the stopcock taken along a centerline of the device in the position as shown in FIG. 4.
Figure 6:
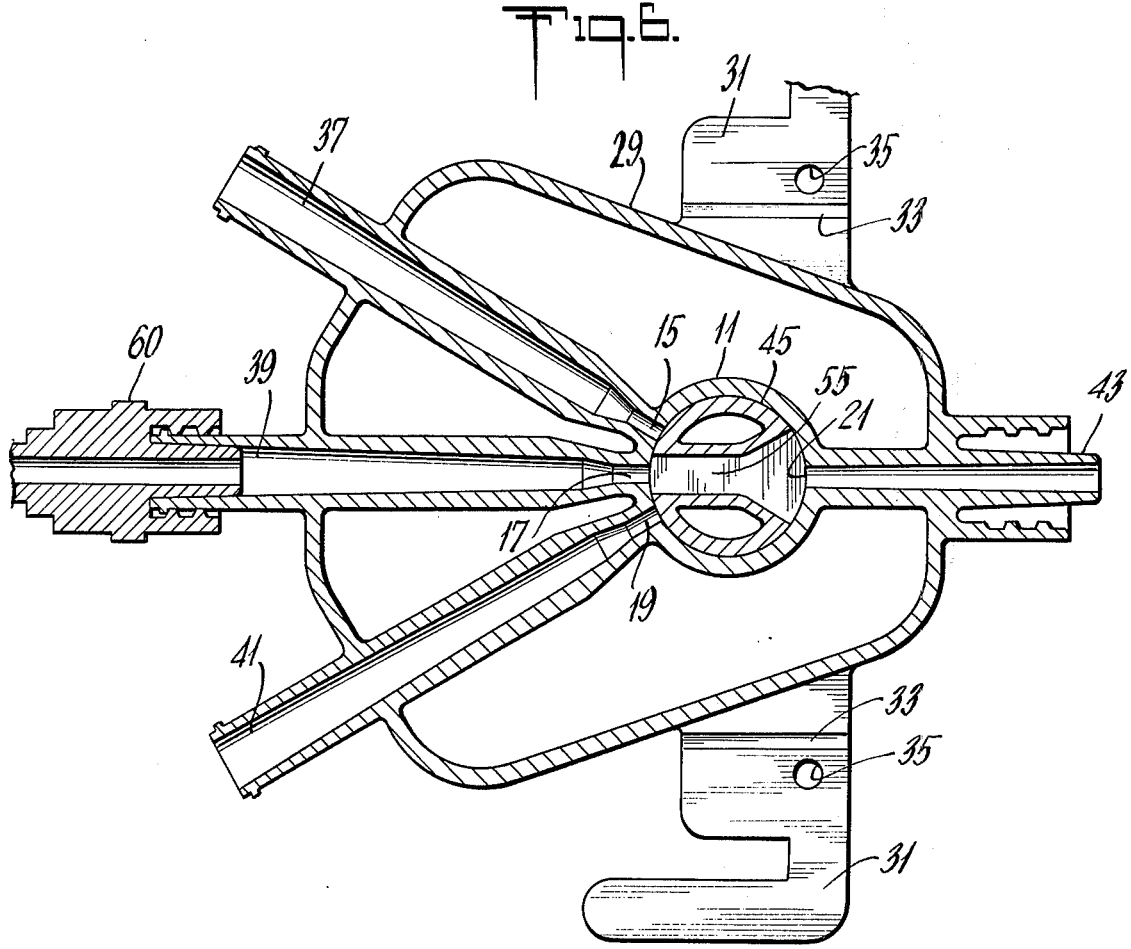
FIG. 6 is a plan sectional view of the stopcock taken through a centerline of the tubing, in the position as shown in FIG. 4.

Cutaway views of the internal passageways of the stopcock are shown in FIGS. 5 and 6. FIG. 7 shows a cross sectional mating of a port and the rotor passageway. The flow pattern in a two fluid mixture position is shown in FIG. 8.

The apparatus as described above, and shown in the drawings was intended to be manufactured in two parts, exclusive of the sealing caps 71. These two parts are the rotor gate 40 which is injection molded out of a single piece of polyethylene; and the body and support member 50 which is injection molded from a single piece of polypropylene.

With such a configuration, voids can be created within the rotor gate 40, below the passageway 55 and within the finger 51, thus saving material without detracting from structural properties. A hollow inside of the round member 49 with its detent 57 and twin stops 59 may be similarly molded. Likewise the body and support member can be molded with a cavity below the support plate 25 which in fact forms the skirt 29. During this process connection tubes 37, 39, 41, 43 are molded as part of the bottom surface of the plate 25. An inexpensive and disposable stopcock is therefore produced. The apparatus, however, can be constructed of other materials and by other processes.

A minimization of flow turbulence is made possible by the straight flow-through design of the stopcock passageway which minimizes fluid change of direction through the stopcock. This minimization of change of direction is made possible by the positioning in close proximity to one another of the inlet ports 15, 17, 19 to one another. This in turn is made practical by the incorporation of connection tubes 37, 39, 41 which places the tubing coupling points away from the body where there is more room to maneuver. It can be concluded from the drawings, especially FIGS. 6 and 8, which show the interior of the stopcock, that any fluid which flows through the stopcock undergoes no individual change of direction greater than 30°. That is to say, by keeping changes in direction of the fluid flow path to 30° or less flow turbulence is minimize.

The accuracy of operation of the device is facilitated by the indicia 61, 63, 65, 67, 69, 71 on the device which can be first visually seen and understood, and then tactilly felt in conjunction with the rotation of the finger 51.

Operation of the stopcock with one hand is made possible by the incorporation of the support structure. It immobilizes the valve body 11 when the tabs 31 are attached to an immobile object, thus permitting the knob 47 to be rotated with a finger and thumb. The skirt 29 spaced a sufficient distance away from the body 11 provides a stable support, i.e., one which does not rock. Tabs 31 being flexible can conform the support structure to a rounded object such as an arm.

Alternatively, when tabs 31 are not used it is possible to grasp the support plate 27, and skirt 29 with the fingers and palm of the hand while turning the knob 47 by its protruding finger 51 with the thumb and finger.

The above description is to be taken as illustrative and not in the limiting sense. Many modifications can be made to the design without deviating from the scope thereof.

What is claimed is:

1. A selection valve for use in the administration of intravenous fluids comprising:
   a body having a cylindrically shaped cavity, said body including at least three inlet ports and an outlet port extending through its cylinder wall; and
   means disposed within said body cavity for selectively connecting any one of said inlet ports with said outlet port, for selectively connecting any two adjacent inlet ports with said outlet port and for selectively closing off, simultaneously, all said inlet ports.

2. The apparatus of claim 1 wherein said connecting means includes a single movable passageway having a rectangular cross section and a substantially straight axis.

3. The apparatus of claim 2 wherein said passageway walls are flared at the outlet port end thereof.

4. The apparatus of claim 3 also including:
   means for maintaining a selected connection and for limiting the operation of said selective connecting means, said maintaining and limiting means being co-operative with said selective connecting means.

5. The apparatus of claim 4 wherein said inlet and outlet port openings and said passage means opening equal to that of a 14-gauge hypodermic needle and larger.

6. The apparatus of claim 5 wherein each of said body inlet ports is spaced at and less than 30° from an adjacent port and wherein said outlet port position is diametrically across from a central point of said inlet port spacing.

7. In a selection valve for use in the administration of intravenous fluids including a body having a cylindrically-shaped cavity, said body having at least three inlet ports and an outlet port extending through its cylindrical wall and means disposed within said body cavity for selectively connecting any one of said inlet ports with said outlet port, for selectively connecting any two adjacent inlet ports with said outlet port and for selectively closing off, simultaneously, all said inlet ports; the improvement comprising:
   an annular groove positioned in the cylindrical wall of said body cavity between said inlet and outlet ports and the top of said cavity; and
   wherein said selective connecting means includes:
   a cylindrically-shaped rotor gate, said rotor gate being insertable, with a tight fit, in the cylindrical cavity of said body, and having a protruding annular ring seating into said body's annular groove when said rotor is in position, said rotor also having a transverse rectangular passageway with one opening being at most 30° of circumferential arc and the other opening being at most 60° of circumferential arc; and
   a circular operator's knob attached to said annular ring end of said rotor, said knob being circumferentially bossed and having a serrated finger protruding in alignment with the passageway of said rotor.

8. The apparatus of claim 7 wherein said maintaining and limiting means includes:
   a curved plate mounted to said body having a plurality of indentations on its curvature, one of which corresponds to each of the fluid passage positions of said rotor;
   a detent from said knob diametrically opposite said serrated finger positioned to engage said indented curved plate when said rotor is positioned in said body; and a pair of stops extending from said knob adapted to abut a respective end of said curved plate and defining the rotational limit of and rotor an knob.

9. The apparatus of claim 8 also including:
a support plate connected to said body;
a skirt extending normally from said plate away from said operating knob a distance greater than the extension of said body, said skirt being located at a periphery spaced from said body;
a plurality of connection tubes attached one each to each of said body input and output ports and to said support plate and said skirt, each of said tubes extending beyond said skirt; and
a plurality of flexible tabs attached to the free end of said skirt and extending outwardly from said skirt.

10. The apparatus of claim 9 wherein said tabs each have a L-shaped arm capable of engagement by adhesive tape and similar securing mediums.

11. The apparatus of claim 10 wherein the free end of each inlet port connection tube has a female Luer fitting, said fittings include flanged locking members; and wherein the free end of said outlet port connection tube has a male Luer fitting, said fitting including flanged locking members.

12. In a selection valve for use in the administration of intravenous fluids, said valve including a body portion having input and output ports, and a movable gate portion cooperating with said body, said gate having a transverse passageway and an operating knob protruding away from said body, the improvement comprising:
a support plate connected to said body portion;
a skirt extending normally from said plate away from said gate operating knob a distance greater than the body portion, said skirt being located at a periphery spaced from said body portion;
a plurality of connection tubes attached one each to each of said body input and output and to said support plate and said skirt, each of said tubes extending beyond said skirt; and
means connected to said skirt for conforming to the surface shape of a mounting object.

13. The apparatus of claim 12 wherein said conforming means includes:
a plurality of folding tabs attached normal to the free end of said skirt and extending outwardly from said skirt.

14. The apparatus of claim 13 also including indicia on said plate surface facing said knob and on said knob, said indicia signifying phases of operation of said selection knob.

15. The apparatus of claim 14 wherein said plate indicia includes:
a sequence of raised numbers, one each over each of said input port connection tubes;
a plurality of raised index points, one each at a midpoint between each tube number; and
a pair of off-set, "off"-labels, located one on each extreme side of said raised numbers and said index midpoints.

16. The apparatus of claim 15 wherein said knob indicia includes:
an arrow on said knob signifying the direction of flow through said gate; and
an outline of the shape and position of said transverse passageway in said gate.

* * * * *